(12) United States Patent
Gudipati et al.

(10) Patent No.: US 6,630,498 B2
(45) Date of Patent: Oct. 7, 2003

(54) EPROSARTAN ARGINYL CHARGE-NEUTRALIZATION-COMPLEX AND A PROCESS FOR ITS PREPARATION AND FORMULATION

(75) Inventors: Manga R Gudipati, Yardley, PA (US); John M Jushchyshyn, Lansdowne, PA (US); Nageswara R Palepu, Millcreek, WA (US); Gopadi M Venkatesh, Blue Brook, OH (US)

(73) Assignee: SmithKline Beecham Corporation, Philadelphia, PA (US)

( * ) Notice: Subject to any disclaimer, the term of this patent is extended or adjusted under 35 U.S.C. 154(b) by 103 days.

(21) Appl. No.: 10/017,873

(22) Filed: Dec. 12, 2001

(65) Prior Publication Data

US 2002/0137943 A1 Sep. 26, 2002

Related U.S. Application Data

(63) Continuation of application No. 09/485,203, filed as application No. PCT/US98/16245 on Aug. 4, 1998, now abandoned.
(60) Provisional application No. 60/054,990, filed on Aug. 6, 1997.

(51) Int. Cl.$^7$ .................. A61K 31/415; C07D 233/64
(52) U.S. Cl. ..................... 514/397; 548/315.1
(58) Field of Search ..................... 548/315.1; 514/397

(56) References Cited

U.S. PATENT DOCUMENTS

| | | | |
|---|---|---|---|
| 5,185,351 A | | 2/1993 | Finkelstein et al. |
| 5,444,080 A | | 8/1995 | Girard et al. |
| 6,420,412 B2 | * | 7/2002 | Palepu et al. ............... 514/397 |
| 6,426,356 B1 | * | 7/2002 | Baxter et al. ............... 514/365 |
| 6,429,222 B2 | * | 8/2002 | Heitsch et al. ............. 514/397 |
| 6,458,963 B1 | * | 10/2002 | Matsuoka et al. ........ 548/315.1 |

* cited by examiner

*Primary Examiner*—Deborah C. Lambkin
(74) *Attorney, Agent, or Firm*—Mary E. McCarthy; Charles M. Kinzig

(57) ABSTRACT

This invention relates to (E)-α-[2-n-butyl-1-[(4-carboxyphenyl)methyl]-1H-imidazol-5-yl]methylene-2-thiophenepropionic acid arginyl charge-neutralization-complex, a process for its production, compositions containing the compound and methods of using the compound to block angiotensin II receptors and to treat hypertension, congestive heart failure and renal failure.

17 Claims, 10 Drawing Sheets

EPROSARTAN ARGINYL CHARGE-NEUTRALIZATION-COMPLEX AND A PROCESS FOR ITS PREPARATION AND FORMULATION

This is a continuation of application Ser. No. 09/485,203 filed Feb. 3, 2000 now abandoned which is a 371 of Application PCT/US98/16245 filed Aug. 4, 1998 which claims benefit to provisional application No. 60/054,990 filed Aug. 6, 1997.

FIELD OF THE INVENTION

This invention relates to a pharmaceutically active compound, a process for its production, compositions containing the compound and methods of using the compound in the treatment of certain disease states in mammals, in particular man. More specifically, the present invention relates to a charge-neutralization-complex of (E)-α-[2-n-butyl-1-[(4-carboxyphenyl)methyl]-1H-imidazol-5-yl]methylene-2-thiophenepropionic acid or its salt form, particularly, the methanesulfonate salt, and L-arginine. Most particularly, this invention relates to a 1:1 to a 1:3 molar charge-neutralization-complex of (E)-α-[2-n-butyl-1-[(4-carboxyphenyl)methyl]-1H-imidazol-5-yl]methylene-2-thiophenepropionic acid or its monomethanesulfonate salt and L-arginine (herein referred to as (E)-α-[2-n-butyl-1-[(4-carboxyphenyl)methyl]-1H-imidazol-5-yl]methylene-2-thiophenepropionic acid arginyl charge-neutralization-complex or eprosartan arginyl charge-neutralization-complex), a wet granulation process for preparing said charge-neutralization-complex, compositions containing this charge-neutralization-complex, and methods of using (E)-α-[2-n-butyl-1-[(4-carboxyphenyl)methyl]-1H-imidazol-5-yl]methylene-2-thiophenepropionic acid arginyl charge-neutralization-complex to block angiotensin II (AII) receptors and to treat hypertension, congestive heart failure and renal failure.

BACKGROUND OF THE INVENTION

The compound (E)-α-[2-n-butyl-1-[(4-carboxyphenyl)methyl]-1H-imidazol-5-yl]methylene-2-thiophenepropionic acid is known by the name eprosartan and its methanesulfate salt is known as eprosartan mesylate. Eprosartan and eprosartan mesylate are the subject of U.S. Pat. No. 5,185,351 (the '351 patent), issued Feb. 9, 1993. This patent discloses in Example 41 a process for making the anhydrous form of (E)-α-[2-n-butyl-1-[(4-carboxyphenyl)methyl]-1H-imidazol-5-yl]methylene-2-thiophenepropionic acid monomethanesulfonate. Additionally, the '351 patent discloses conventional techniques for formulating (E)-α-[2-n-butyl-1-[(4-carboxyphenyl)methyl]-1H-imidazol-5-yl]methylene-2-thiophenepropionic acid monomethanesulfonate and Examples 108–111 specifically detail the preparation of certain formulations. This compound is claimed to have utility in blocking angiotensin II receptors and to be useful in the treatment of hypertension, congestive heart failure and renal failure.

Human clinical studies indicate (E)-α-[2-n-butyl-1-[(4-carboxy phenyl)methyl]-1H-imidazol-5-yl]methylene-2-thiophenepropionic acid monomethanesulfonate to be safe and well tolerated even up to doses of 800 mg per day. The time to maximum concentration is between 1 to 2.5 hours in fasted state and 2.5–4 hours in fed state. (E)-α-[2-n-butyl-1-[(4-carboxyphenyl)methyl]-1H-imidazol-5-yl]methylene-2-thiophenepropionic acid monomethanesulfonate exhibits a mean absolute bioavailability of approximately 13%.

Surprisingly, it has been found that the arginine charge-neutralization-complex of (E)-α-[2-n-butyl-1-[(4-carboxyphenyl)methyl]-1H-imidazol-5-yl]methylene-2-thiophenepropionic acid or its monomethanesulfonate salt has increased lipophilicity, better dissolution profile and increased in vitro permeability through rabbit colon, when compared to the monomethanesulfonate salt. This is particularly important when formulating (E)-α-[2-n-butyl-1-[(4-carboxyphenyl)methyl]-1H-imidazol-5-yl]methylene-2-thiophenepropionic acid or its monomethanesulfonate salt for therapeutic use.

SUMMARY OF THE INVENTION

The present invention provides a novel charge-neutralization-complex of L-arginine and (E)-α-[2-n-butyl-1-[(4-carboxyphenyl)methyl]-1H-imidazol-5-yl]methylene-2-thiophenepropionic acid or its monomethanesulfonate salt in pharmaceutical compositions for the treatment of diseases in which blockade of angiotensin II receptors is indicated, for example, in the treatment of hypertension, congestive heart failure and renal failure.

The present invention also provides a process for preparing (E)-α-[2-n-butyl-1-[(4-carboxyphenyl)methyl]-1H-imidazol-5-yl]methylene-2-thiophenepropionic acid arginyl charge-neutralization-complex during wet granulation of the anhydrous form of (E)-α-[2-n-butyl-1-[(4-carboxyphenyl)methyl]-H-imidazol-5-yl]methylene-2-thiophenepropionic acid monomethanesulfonate with water in the presence of L-arginine.

Figure 1A:
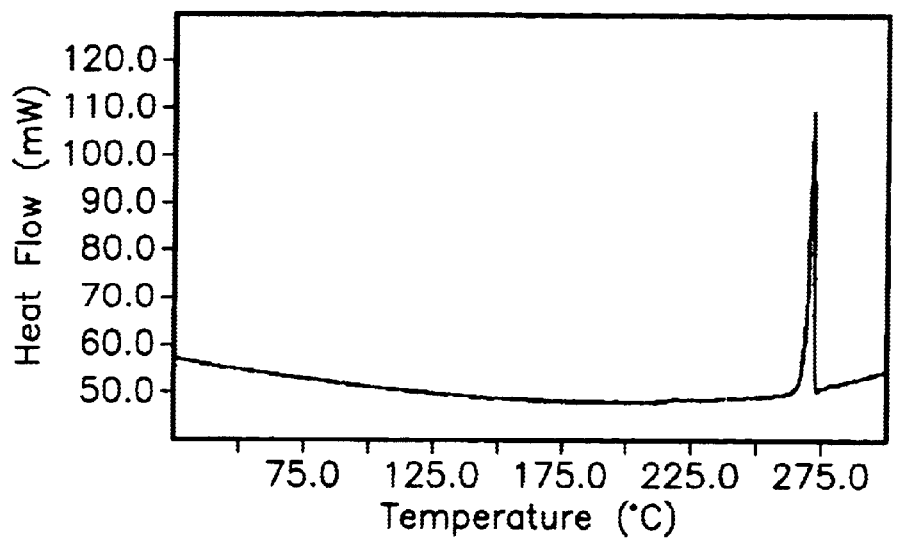
FIGS. 1 and 2 show, respectively, the differential scanning calorimetric (DSC) thermogram and the powder X-ray diffraction (XRD) pattern of the anhydrous form of (E)-α-[2-n-butyl-1-[(4-carboxyphenyl)methyl]-1H-imidazol-5-yl]methylene-2-thiophenepropionic acid, its monomethane sulfate salt and L-arginine. The anhydrous form of (E)-α-[2-n-butyl-1-[(4-carboxyphenyl)methyl]-1H-imidazol-5-yl]methylene-2-thiophenepropionic acid [referred to as eprosartan zwitterion] exhibits a single thermal event, a melting endotherm at about 269° C., followed by decomposition of the drug substance [FIG. 1 (a)]. The anhydrous form of (E)-α-[2-n-butyl-1-[(4-carboxyphenyl)methyl]-1H-imidazol-5-yl]methylene-2-thiophenepropionic acid monomethanesulfonate [referred to as eprorsartan mesylate or its methanesulfonate salt] exhibits a single thermal event, a melting endotherm at about 251° C., followed by decomposition of the drug substance [FIG. 1(b)]. No significant weight losses prior to melting are observed in their thermogravimetric analysis, suggesting that this compounds do not contain significant quantities of surface adsorbed water and/or residual solvents. L-arginine (the sample is not 100% L isomer) appears to melt at 246° C., followed by severe degradation of the salt. A small endotherm at about 223° C., which represents the melting of the arginine isomer, is also observed [FIG. 1(c)]. The powder X-ray diffraction patterns [FIG. 2] exhibit characteristic diffraction lines corresponding to 2θ values of 6.5, 7.25, 16.6, 21.8, 22.7 and 27 degrees for the zwitterion [FIG. 2(a)] and 7, 14, 18.9, 22.2 and 29 degrees for the mesylate salt [FIG. 2(b)]. L-Arginine exhibits characteristic X-ray diffraction peaks at 18, 18.7, 19.2, 22.8 and 27.2° 2θ values [FIG. 2(c)].
Figure 1B:
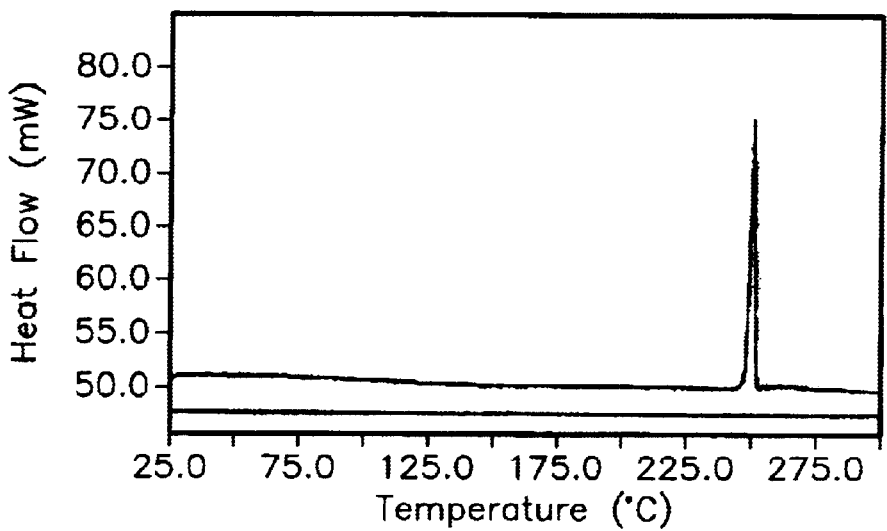
Figure 1C:
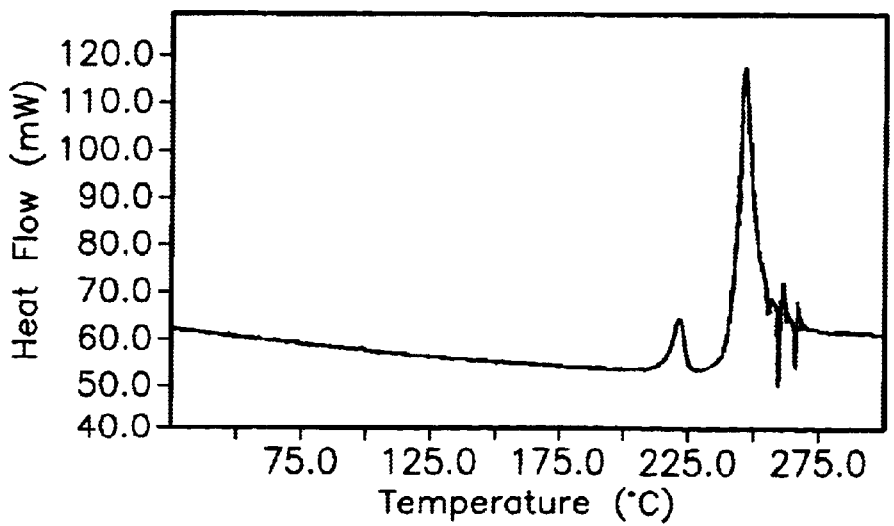
Figure 2A:
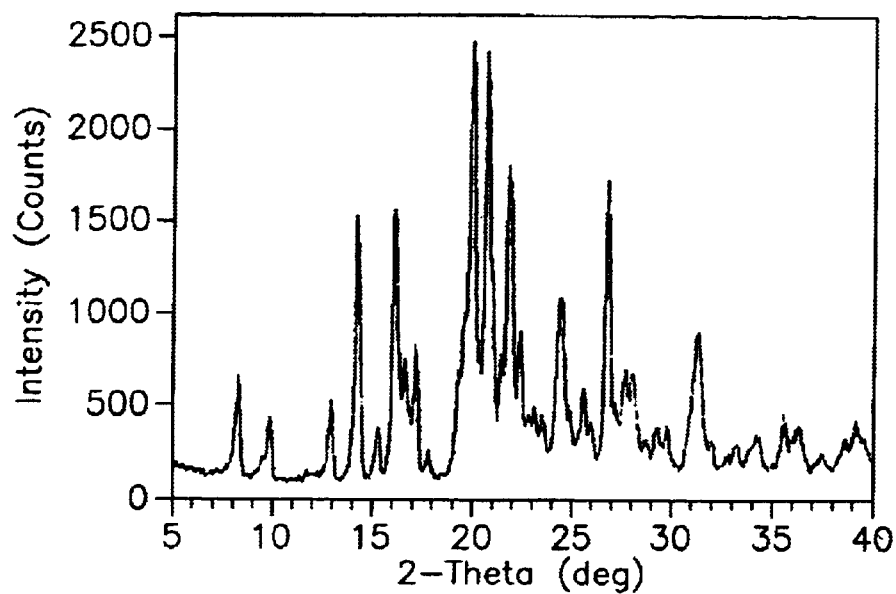
Figure 2B:
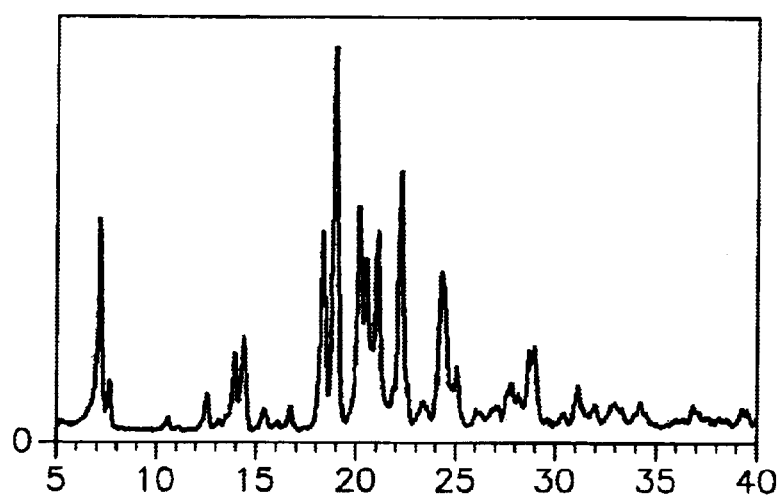
Figure 2C:
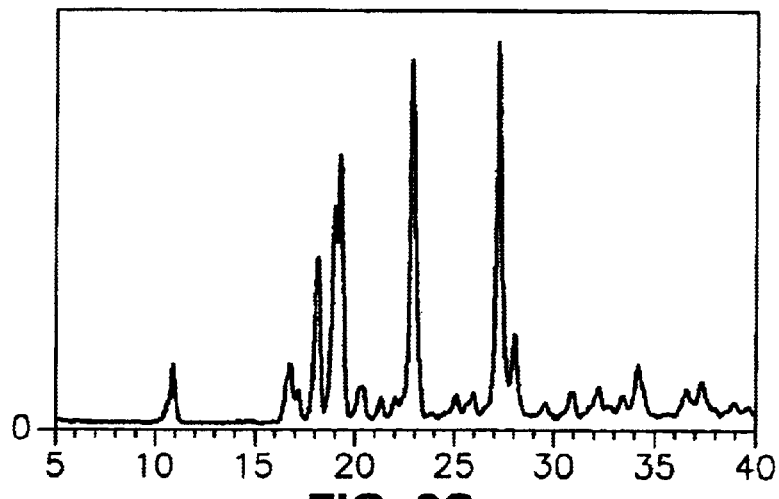
Figure 3A:
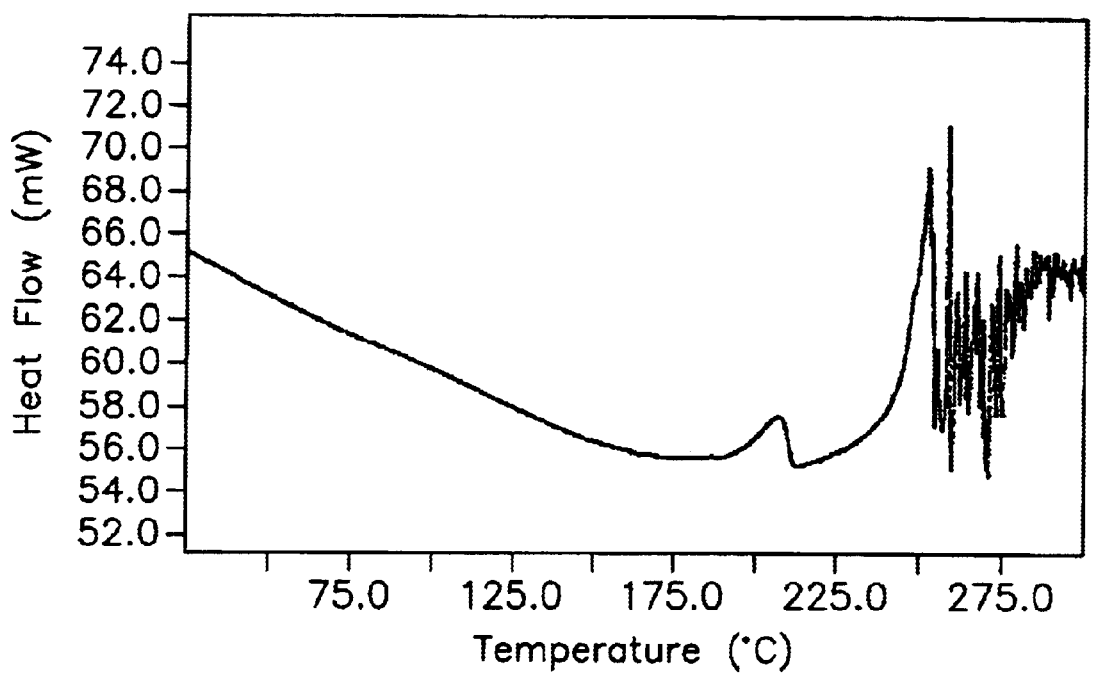
Figure 3B:
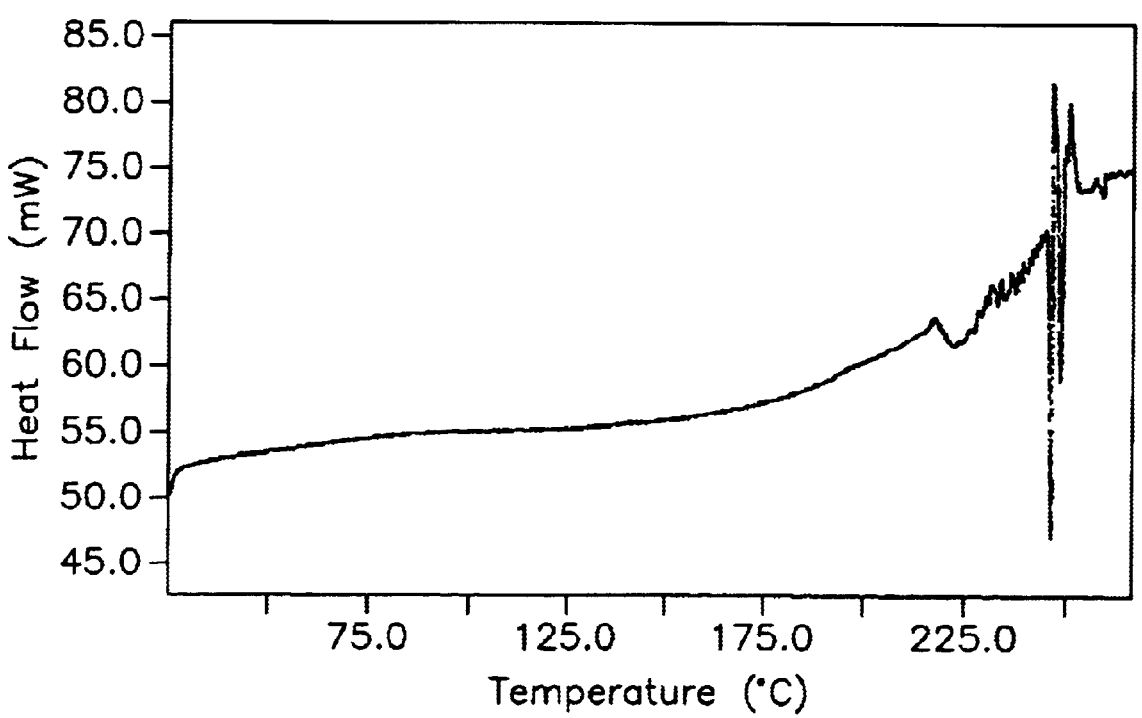
Figure 3C:
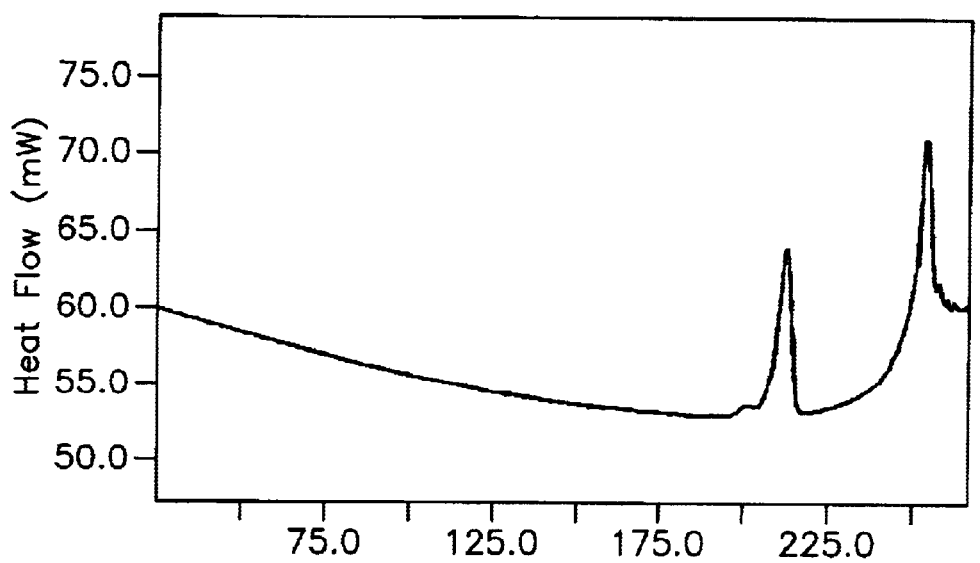
Figure 3D:
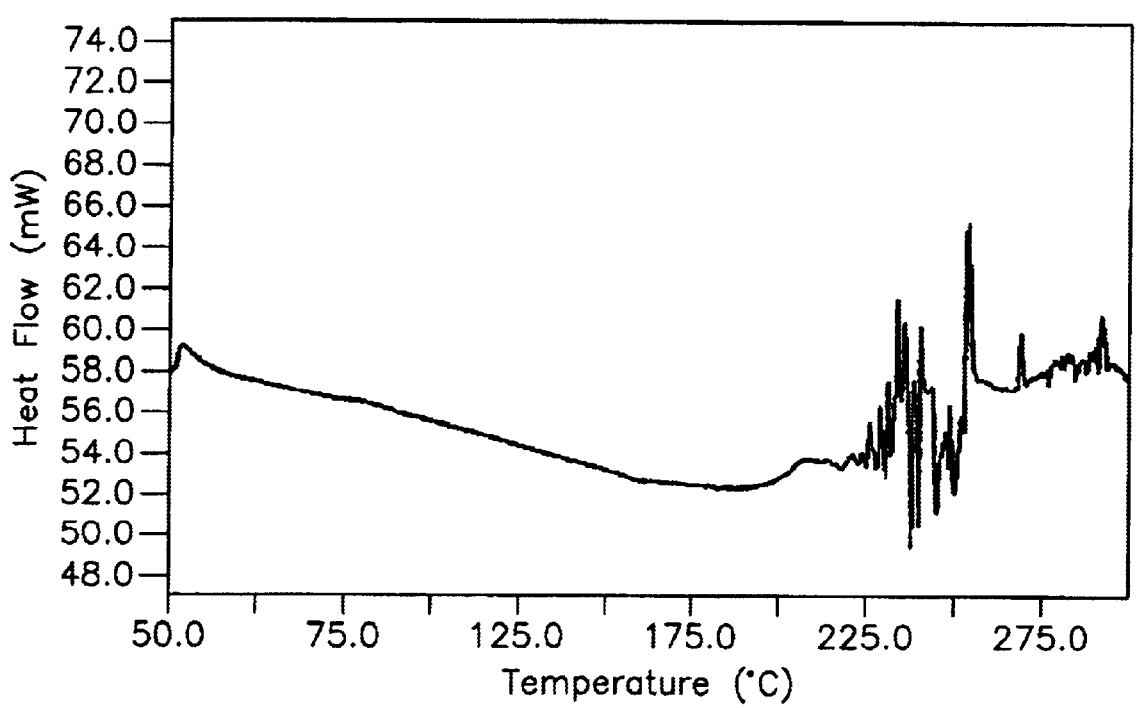
Figure 4A:
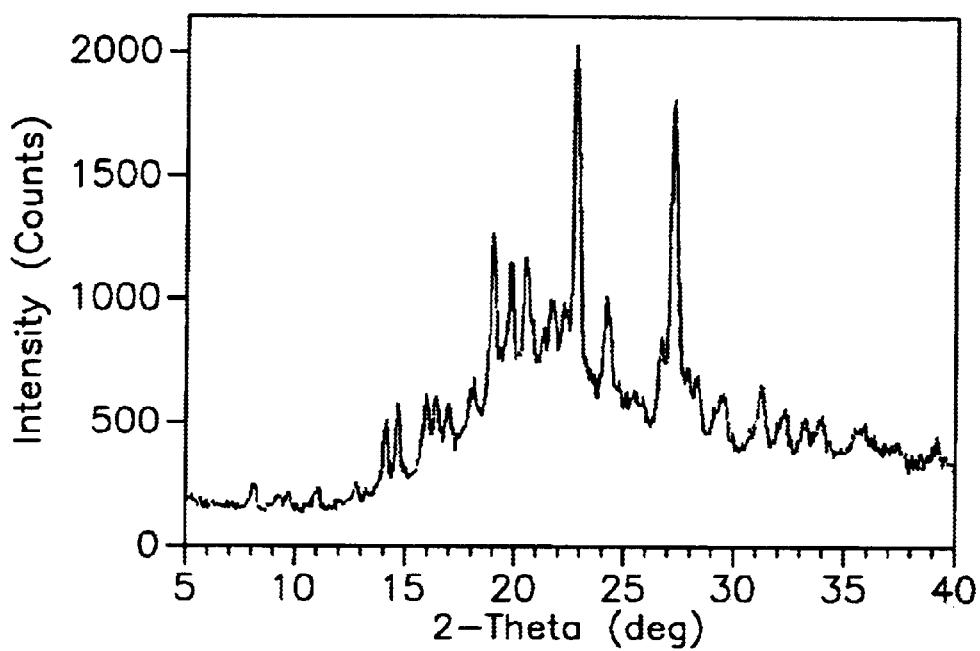
Figure 4B:
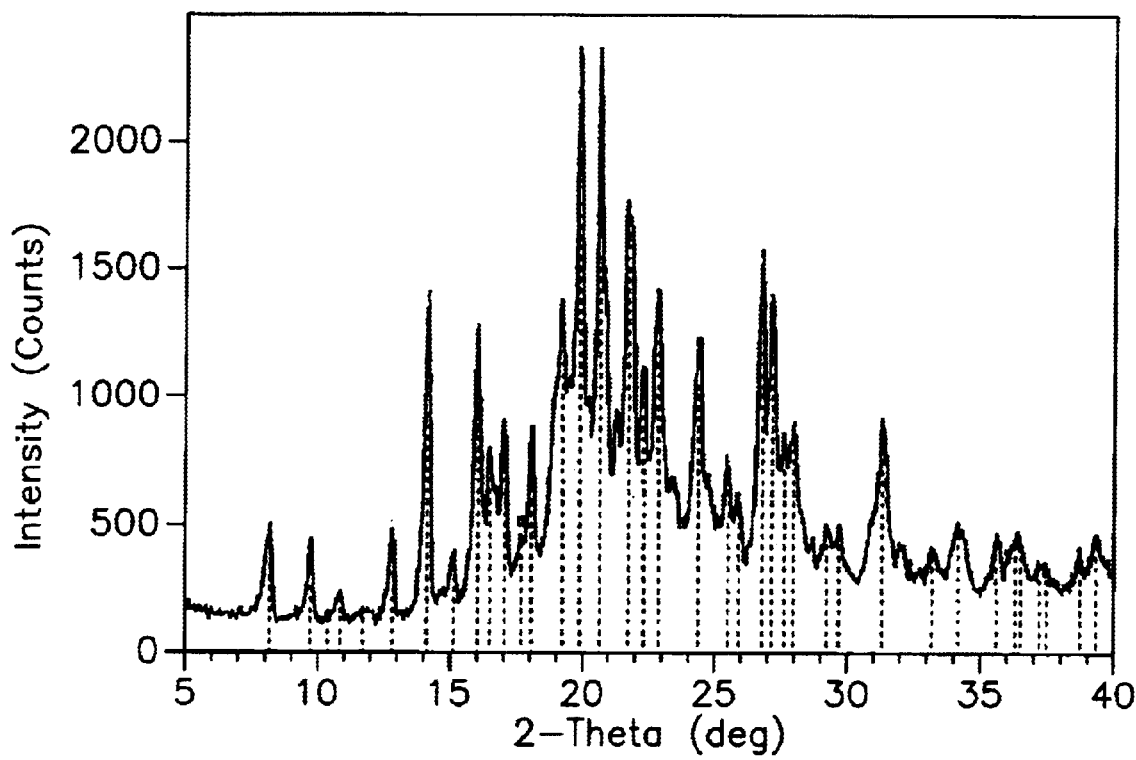
Figure 4C:
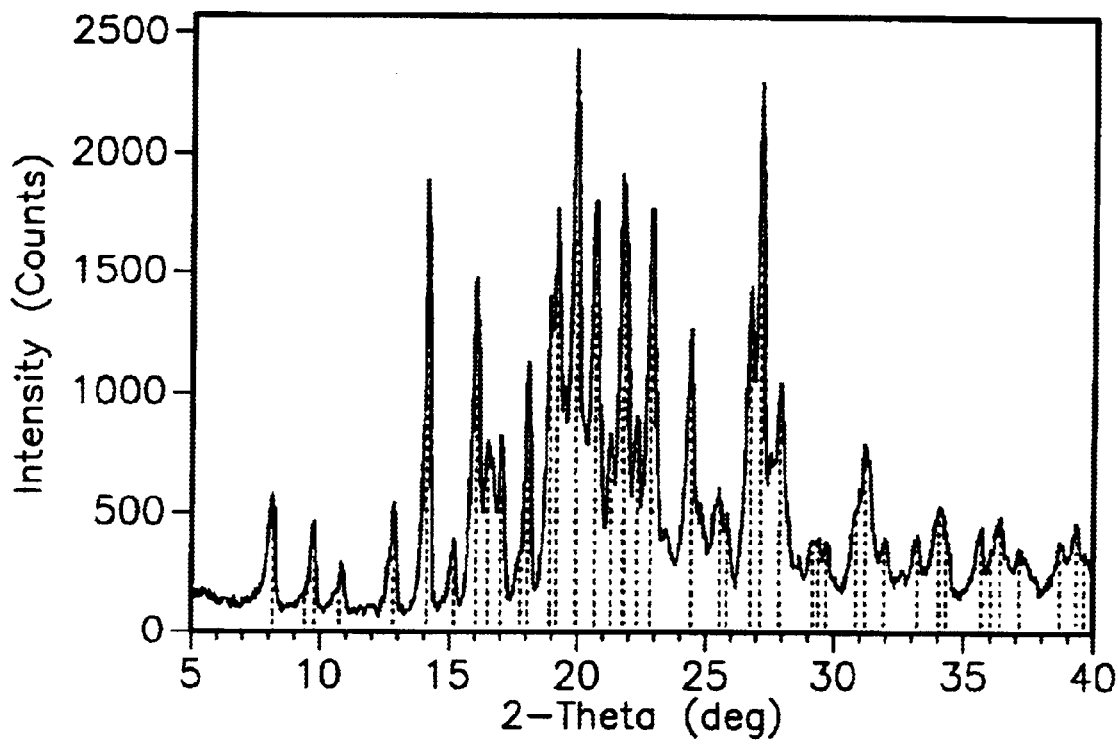
Figure 4D:
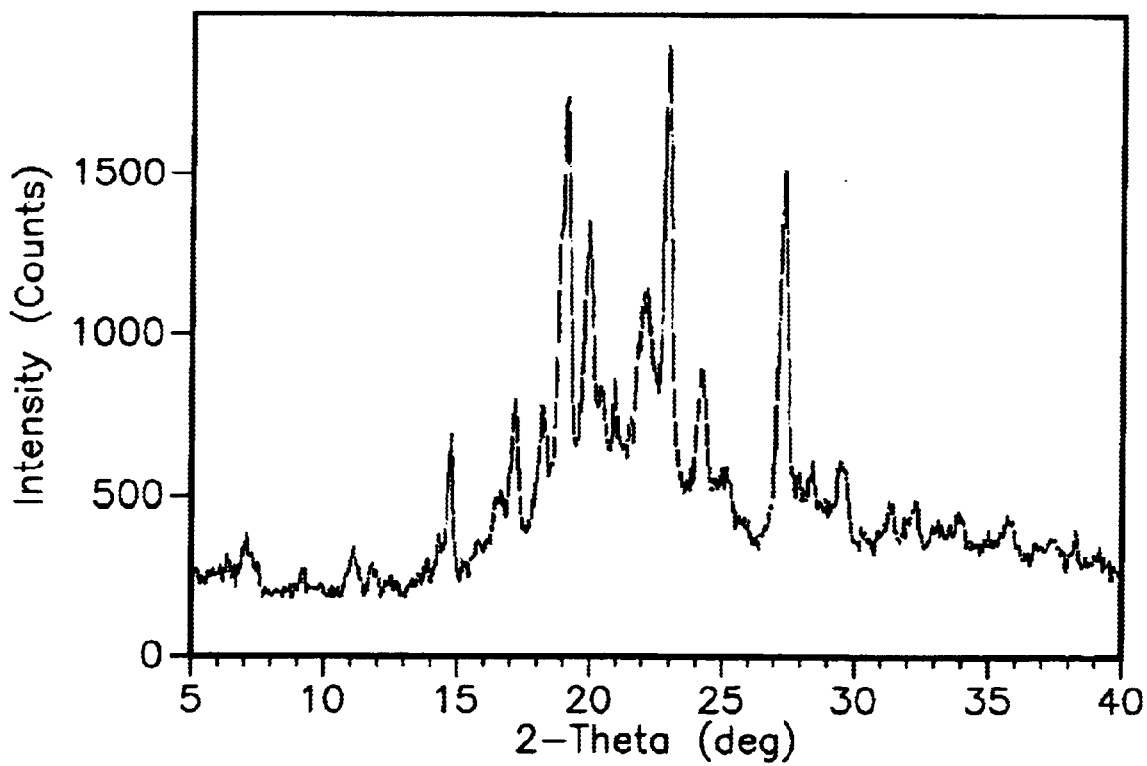
Figure 5A:
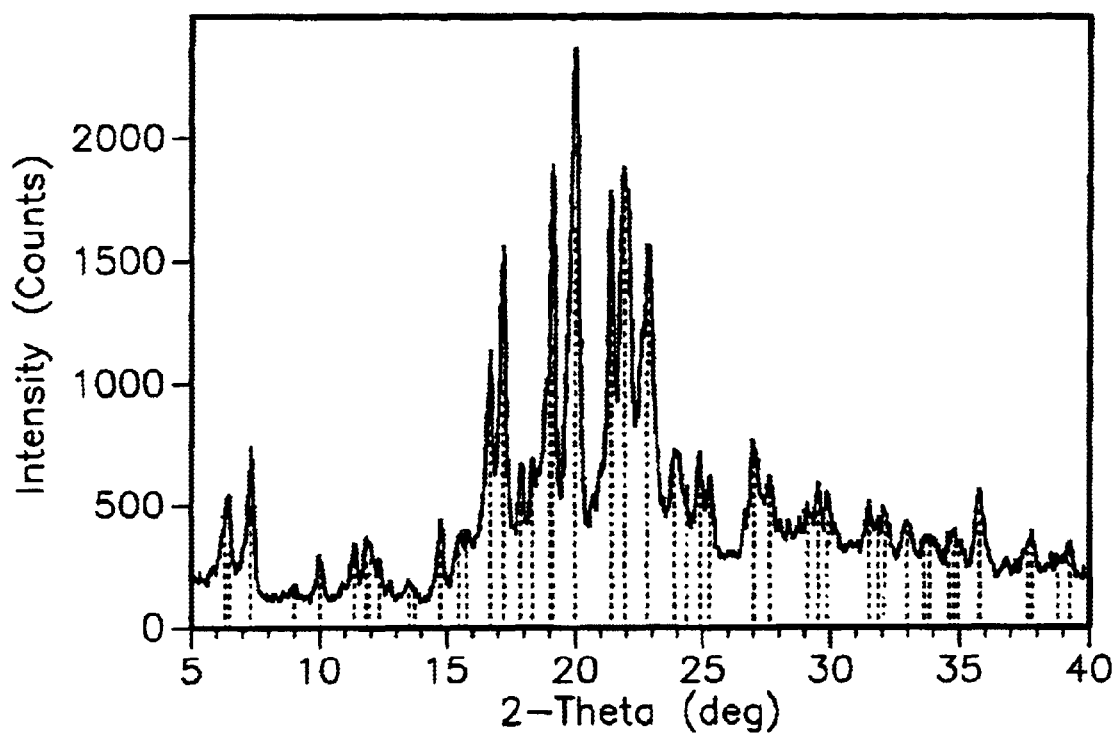
Figure 5B:
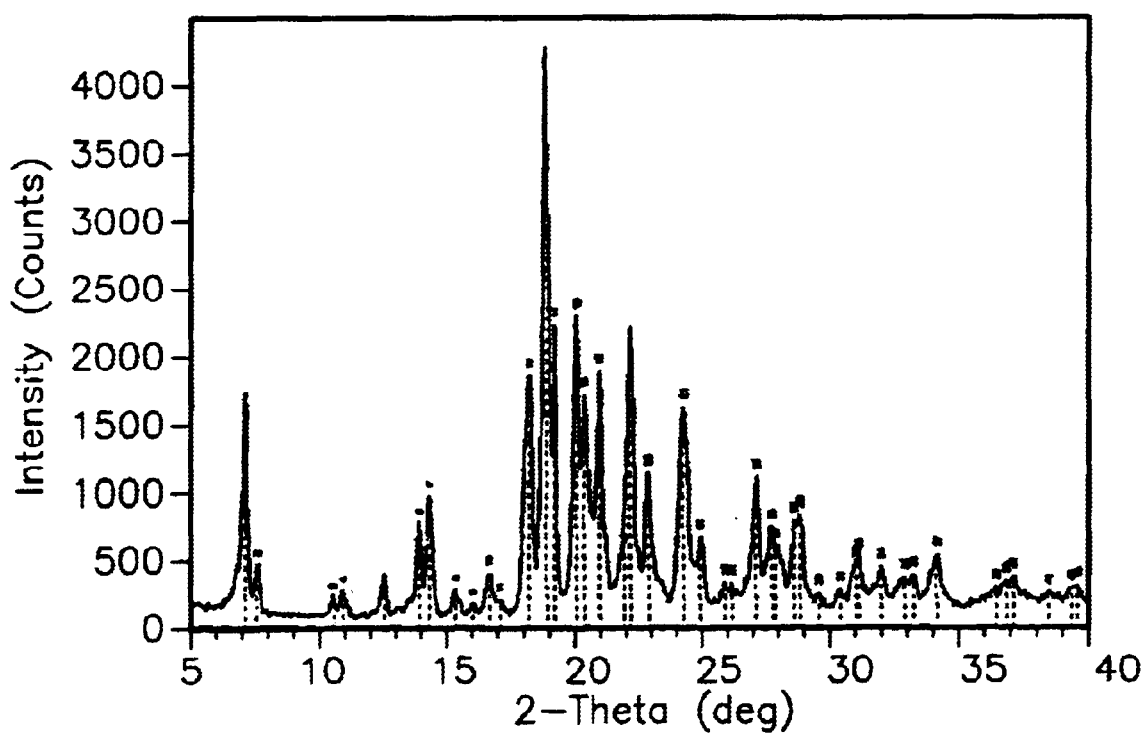

The DSC thermograms of 1:1 molar arginine-zwitterion charge-neutralization complex [FIG. 3(a)] and 1:2 molar arginine-zwitterion charge-neutralization complex [FIG. 3(b)] and of 1:1 molar arginine-mesylate salt [FIG. 3(c)] and 1:3 molar arginine-mesylate salt charge-neutralization complex [FIG. 3(d)] are presented in FIGS. 3(a)–(d). The 1:1 and 1:2 molar charge-neutralization-complexes of L-arginine-zwitterion show small endotherms at about 213° C. The 1:1 and 1:3 molar arginine-methanesulfonate salt charge-neutralization-complex exhibit two endotherms at about 213 and 252° C. The XRD patterns of arginine charge-neutralization complexes shown in FIG. 4(a), FIG. 4(b), FIG. 4(c), and FIG. 4(d) wherein (a) is 1:1 molar zwitterion-arginine, (b) is 1:2 molar zwitterion-arginine, (c) is 1:1 molar mesylate-arginine and (d) is 1:3 molar mesylate-arginine are significantly different from those of their 1:1 molar physical blends [FIG. 5](a) and FIG. 5(b) wherein (a) is 1:1 molar zwitterion-arginine and (b) is 1:1 molar mesylate-arginine.

Figure 6:
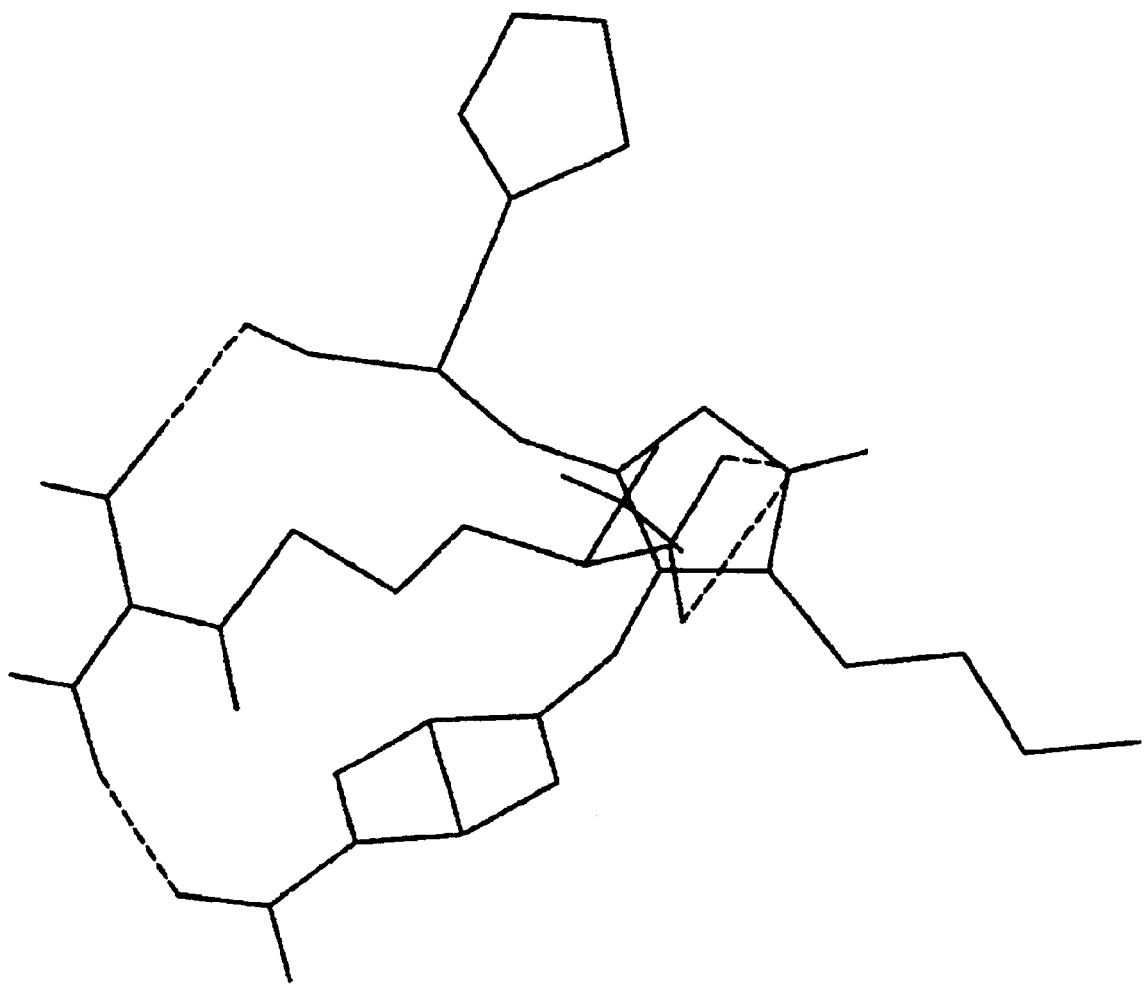

FIG. 6 illustrates the pictorial representation of the molecular model of the eprosartan arginine charge-neutralization-complex generated by energy minimization.

Figure 7:
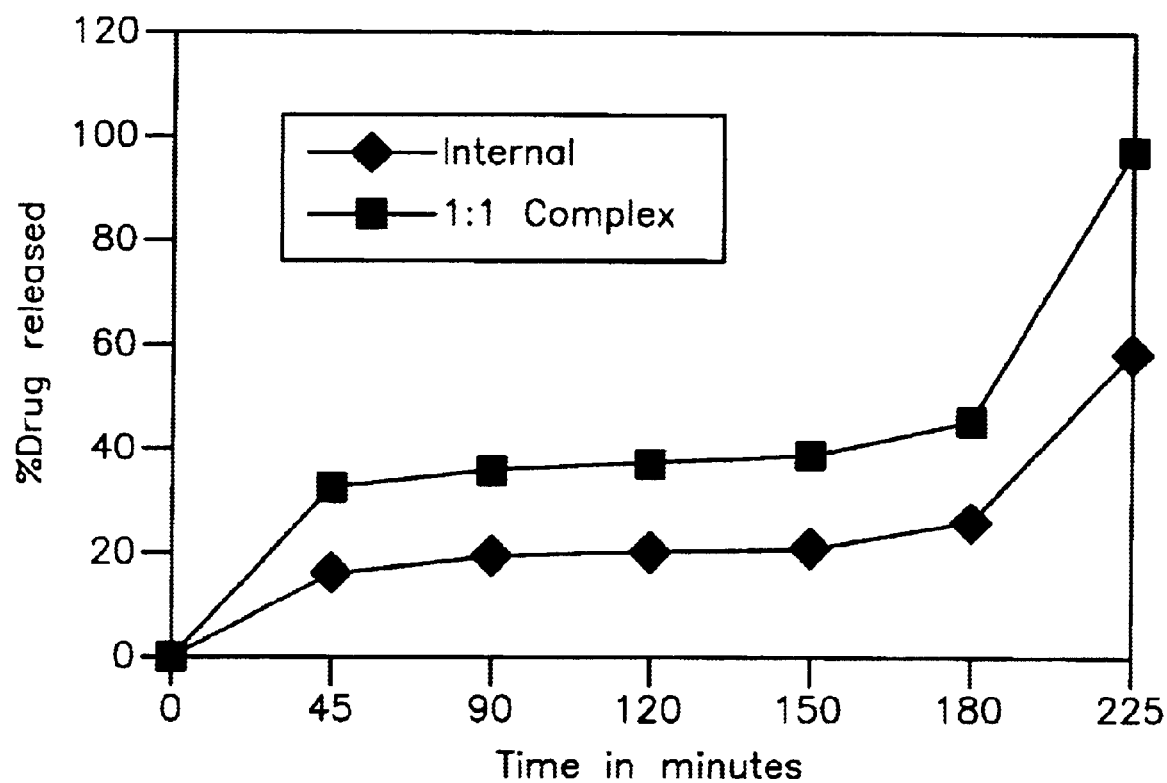

FIG. 7 is an illustration of the dissolution profile for eprosartan and its arginyl charge-neutralization-complex.

Figure 8:
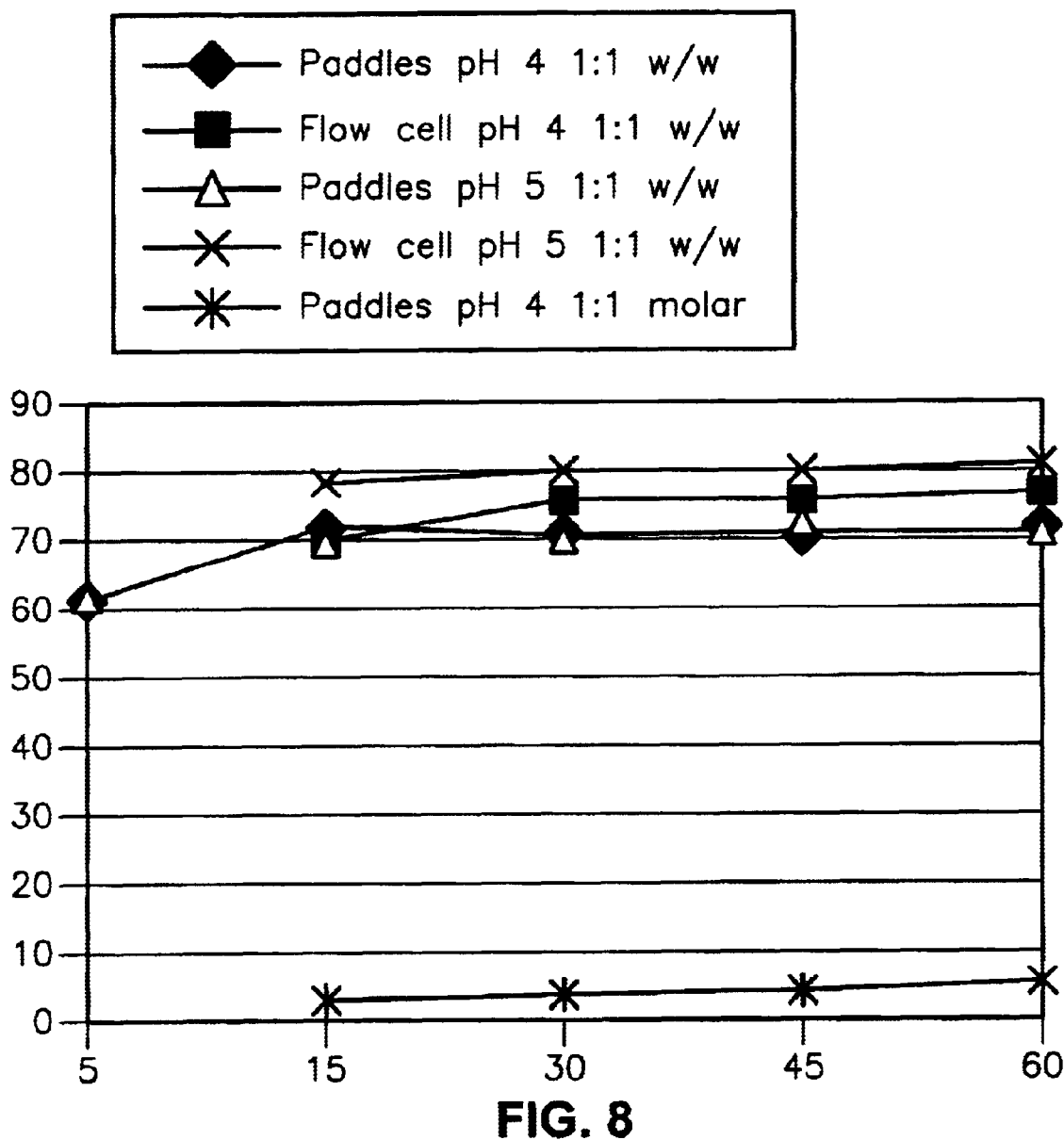

FIG. 8 illustrates the comparative dissolution data of 200 mg eprosartan:arginine granules in pH 4 and pH 5 environments.

DETAILED DESCRIPTION OF THE INVENTION (E)-α-[2-n-Butyl-1-[(4-carboxyphenyl)methyl]-1H-imidazol-5-yl]methylene-2-thiophenepropionic acid monomethanesulfonate is known to exist in an anhydrous form. This compound has the following structure:

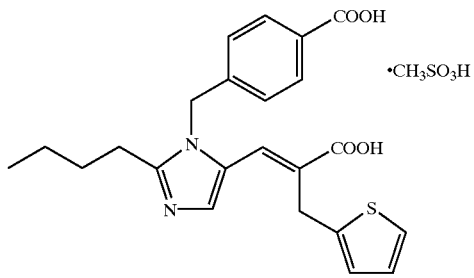

(E)-α-[2-n-Butyl-1-[(4-carboxyphenyl)methyl]-1H-imidazol-5-yl]methylene-2-thiophenepropionic acid monomethanesulfonate, eprosartan mesylate, is claimed in U.S. Pat. No. 5,185,351. Reference should be made to said patent for its full disclosure, including the methods of preparing and using this compound. The entire disclosure of the '351 patent is incorporated herein by reference.

Human clinical studies indicate (E)-α-[2-n-butyl-1-[(4-carboxy phenyl)methyl]-1H-imidazol-5-yl]methylene-2-thiophenepropionic acid monomethanesulfonate to be safe and well tolerated even up to doses of 800 mg per day. (E)-α-[2-n-Butyl-1-[(4-carboxyphenyl)methyl]-1H-imidazol-5-yl]methylene-2-thiophenepropionic acid monomethanesulfonate exhibits low and variable bioavailability with a mean absolute bioavailability of approximately 13%. It is perceived that the low and variable bioavailability is probably due to an absorption window between the duodenum and the jejunum.

Eprosartan is an ampiphilic molecule containing two acidic (allylic carboxylic acid, AH; and phenylic carboxylic acid, PH) and one basic (imidazole, I) functional groups. The ionization behavior of the drug can be illustrated as follows:

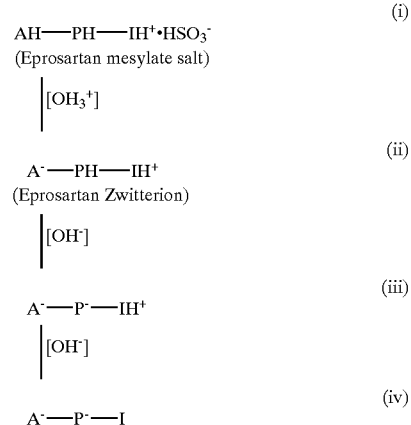

At lower pH (below 2) the imidazole nitrogen will be protonated (i). As the pH increases, the allylic catboxylic group will be deprotonated (iii). Estimated $pK_a$ of the allylic craboxilic group is 2.9. As the pH increases further, the phenylic carboxylic group will be depronated (iv) followed by the deprotonation of the protonated imidazole group (v). The estimated $pK_a$ of the phenylic carboxylic group is 5.9 and that of imidazole group is 6.8. According to the pH-partitioning theory of absorption, only unionized species (ii) or ion-neutral (iii) will be absorbed by passive diffusion. Therefore, by ion-pairing or charge-neutralization-complexing with ampiphiles having ionic characteristics opposite to that of the drug, the concentration of the unionized or ion-neutral species can be maximized and, hence, the absorption is improved. Basic amino acids such as arginine, lysine, omithine possess such desirable characteristics. Arginine was selected for evaluation as a bioenhancer because it is an amphoteric substance with ionic characters opposite to the drug at most of the biologically relevant pHs, thereby increasing the possibility of a strong association either as an ion-pair or as a charge-neutralization-complex.

In accordance with the present invention, it has been found that a stable charge-neutralization-complex of (E)-α-[2-n-butyl-1-[(4-carboxyphenyl)methyl]-1H-imidazol-5-yl] methylene-2-thiophenepropionic acid is produced in situ during the wet granulation processing of the anhydrous form of said compound with water in the presence of L-arginine. The arginine charge-neutralization-complex of eprosartan is then used in the preparation of solid dosage forms (e.g., capsules and tablets) of the drug. The granules containing (E)-α-[2-n-butyl-1-[(4-carboxy-phenyl)methyl]-1H-imidazol-5-yl]methylene-2-thiophene-propionic acid arginyl charge-neutralization-complex may be produced by mixing the anhydrous form of the compound with arginine or any such similar amphiphilic substance and one or more pharmaceutically acceptable carriers, followed by granulation with water.

The arginine charge-neutralization-complex of (E)-α-[2-n-butyl-1-[(4-carboxyphenyl)methyl]-1H-imidazol-5-yl] methylene-2-thiophenepropionic acid or its monomethanesulfonate formed in situ during the wet granulation process is prepared using a planetary/high shear granulator for preparing solid dosage forms of the anhydrous form of said compound with water in the presence of arginine. When a slugging press or a roller compactor is used to prepare dry granules or a fluid bed granulator is used for the the preparation of the granules to be incorporated into solid dosage forms, the arginine/eprosartan charge-neutralizationcomplex is formed only on contact with water or body fluid, and the charge-neutralization-complex dissolves in the medium.

The molar ratio of (E)-α-[2-n-butyl-1-[(4-carboxyphenyl)-methyl]-1H-imidazol-5-yl]methylene-2-thiophenepropionic acid or its methanesulfate salt to arginine varies from 1:1 to 1:5, most preferably the molar ratio varies from 1:1 to 1:3.

The nature of the complex of arginine and eprosratan or eprosartan mesylate (a true complex or a true salt) is not well understood. For example, it is conceiveable that a true salt or a complex is formed between arginine and eprosartan methanesulfonate, and additional arginine, if present, which is free, helps to rapidly dissolve the charge-neutralization-complex previously formed or in-situ formed on contact with water or body fluid, and maintain it in the solution during dilution. Additional arginine present in any dosage form may further enhance solution stability in the varying pH environment of the gastrointestinal tract, and, hence, may enhance the bioavailability of the bioactive material.

(E)-α-[2-n-butyl-1-[(4-carboxyphenyl)methyl]-1H-imidazol-5-yl]methylene-2-thiophene-propionic acid arginyl charge-neutralization-complexes of this invention, prepared by mixing eprosartan zwitterion or eprosartan mesylate and L-arginine at different molar ratios, are characterized by the data shown in FIGS. 3 and 4.

In addition, the charge-neutralization-complex formation is further characterized by molecular modeling and ultraviolet spectroscopy. FIG. 6 illustrates the pictorial representation of the molecular model (1:1 molar zwitterion-arginine complex) generated by energy minimization. The model indicates a strong association of (E)-α-[2-n-butyl-1-[(4-carboxyphenyl)-methyl]-1H-imidazol-5-yl]methylene-2-thiophene-propionic acid and L-arginine through hydrogen bonding between the two carboxylic groups of the drug to the guanidino group of arginine and a strong electrostatic interaction between the imidazole nitrogen of the drug and the carboxylic group of arginine. A spectral shift is observed in the ultraviolet spectra of the drug arginine charge-neutralization-complex compared to the drug alone from $\lambda_{max}$ of 274 to 306. The charge-neutralization-complex is found to be more lipophilic than the anhydrous drug substance as evidenced by the increased solubility in octanol; 1.023 mg/mL for the charge-neutralization-complex as compared to 0.494 mg/mL for the anhydrous drug substance.

Evaluation of the granules of (E)-α-[2-n-butyl-1-[(4-carboxyphenyl)methyl]-1H-imidazol-5-yl]methylene-2-thiophene-propionic acid arginyl charge-neutralization-complex produced by the methods of the instant invention has shown improved in vitro dissolution profile compared, when to the granules of (E)-α-[2-n-butyl-1-[(4-carboxy phenyl)methyl]-1H-imidazol-5-yl]methylene-2-thiophenepropionic acid monomethanesulfonate. A flow through dissolution apparatus at 8 mL/min flow rate, 37° C. and the following pH gradient

| pH | time | Composition |
|---|---|---|
| 1.2 | 45 min | SGF |
| 3.0 | 45 min | 0.05M phosphate buffer |
| 4.0 | 30 min | 0.05M phosphate buffer |
| 5.0 | 30 min | 0.05M phosphate buffer |
| 6.0 | 30 min | 0.05M phosphate buffer |
| 7.5 | 45 min | 0.05M phosphate buffer | was used to give the results of the flow through dissolution study which are summarized in the following table.

TABLE 1

Summary of the flow through dissolution data of Eprosartan and its arginyl charge-neutralization-complex

| | Percent of Eprosartan dissolved from the granules | |
|---|---|---|
| Time (min) | Eprosartan granules | Arginyl charge-neutralization-complex |
| 0 | 0.00 | 0.00 |
| 45 | 17.77 | 32.81 |
| 90 | 19.43 | 35.82 |
| 120 | 19.64 | 36.24 |
| 150 | 20.16 | 37.44 |
| 180 | 24.05 | 46.70 |
| 225 | 58.52 | 100.63 |

FIG. 7 is an illustration of the dissolution profile for eprosartan mesylate and its arginyl charge-neutralization-complex.

The mucosal to serosal permeability of (E)-α-[2-n-butyl-1-[(4-carboxy phenyl)methyl]-1H-imidazol-5-yl]methylene-2-thiophenepropionic acid monomethane-sulfonate through rabbit colon increased 50% in the presence of L-arginine as a solution compared to (E)-α-[2-n-butyl-1-[(4-carboxy phenyl)methyl]-1H-imidazol-5-yl]methylene-2-thiophenepropionic acid monomethane-sulfonate alone indicating increased lipophilicity and passive diffusion of (E)-α-[2-n-butyl-1-[(4-carboxy phenyl)methyl]-1H-imidazol-5-yl]methylene-2-thiophenepropionic acid arginyl charge-neutralization-complex or ion-pair in the solution.

According to the instant invention, the charge-neutralization-complex formation is usually complete in about 2–10 minutes using a high shear wet granulation process in the preparation of solid dosage forms of (E)-α-[2-n-butyl-1-[(4-carboxyphenyl)-methyl]-1H-imidazol-5-yl]methylene-2-thiophene-propionic acid monomethane-sulfonate anhydrate. The granulation thus prepared, which contains the drug substance in the arginyl charge-neutralization-complex form, can be dried, while keeping the drug substance in the charge-neutralization-complex form.

The process for preparing the solid dosage form containing the compound comprises: (i) producing granules containing (E)-α-[2-n-butyl-1-[(4-carboxy-phenyl)methyl]-1H-imidazol-5-yl]methylene-2-thiophene-propionic acid in its arginine charge-neutralization-complex form in the presence of water, arginine and/or one or more pharmaceutically acceptable carriers and (ii) blending said granules with other pharmaceutically acceptable carriers to be filled into capsules or compressed into tablets exhibiting immediate release (100% release in a short period of time in a suitable dissolution medium) or modified release (sustained release or delayed release) profiles. This process for the preparation of solid dosage forms containing (E)-α-[2-n-butyl-1-[(4-carboxyphenyl)methyl]-1H-imidazol-5-yl]methylene-2-thiophene-propionic acid arginyl charge-neutralization-complex comprises the in situ formation of a stable charge-neutralization-complex during wet granulation, said formation optionally facilitated and stabilized by an excipient. Complete charge-neutralization-complexation takes place in about 2 minutes to 1 hour, preferably in about 2–10 minutes.

In order to produce granules containing (E)-α-[2-n-butyl-1-[(4-carboxy-phenyl)methyl]-1H-imidazol-5-yl]

methylene-2-thiophenepropionic acid in its arginine charge-neutralization-complex, the anhydrous form of the compound and L-arginine are well mixed with or without pharmaceutically acceptable carriers, such as fillers, diluents, disintegrants and binders, granulated with water and dried to a predetermined water content (loss on drying). According to the insatnt invention, arginine should be present from about 1% to about two times the weight of eprosartan. Any combination: of pharmaceutically acceptable carriers, e.g. diluents, fillers, binders and disintegrants, in desired proportions may be utilized in accordance with the wet granulation process of the present invention. The carriers commonly used in pharmaceutical industry are well described in the literature [refer to the Handbook of Pharmaceutical Carriers, A. Wade and P. J. Weller (Editors), American Pharmaceutical Association (1994)]. Pharmaceutically acceptable fillers and diluents include, but are not limited to, the following: lactose (hydrous as well as anhydrous), starch [unmodified (corn starch) or modified (for example, Starch 1500 available from Colorcon)], mannitol, sorbitol, cellulose, inorganic sulfates and phosphates. Disintegrants include, but are not limited to, the following: sodium starch glycolate, sodium carmellose and crosslinked polyvinyl pyrrolidone, and binders include, but are not limited to, the following: gelatin, corn starch, modified starch (Starch 1551, pregelatinized starch), hydroxypropyl methyl cellulose (HPMC) and hydroxypropyl cellulose (HPC), sodium carboxy methyl cellulose. Examples of carriers suitable for modified release applications include, but are not limited to, the following: high molecular weight HPMCs, polymethacrylate polymers known as Eudragits, polyethylene oxide, Polyox® (Union Carbide Corporation), modified ethyl cellulose, Surelease® (Colorcon), crosslinked acrylic acid polymers, Carbopol® (BF Goodrich Speciality Chemicals) and waxy materials, such as glyceryl behenate (Compritol®, glyceryl palmitostearate (Precirol®), and Gelucires® [all from Gattefosse S.a., France] and carnauba wax.

Preferably, the pharmaceutically acceptable carriers used as binders, diluents and fillers during the wet granulation process of this invention are lactose, mannitol, sorbitol, starch (corn starch, soluble starch, or Starch 1551), gelatin, xanthan gum, sodium alginate, Povidone (PVP), and microcrystalline or powdered cellulose, each one of which may act as a facilitator in the formation of a stable arginyl charge-neutralization-complex of eprosartan. More preferably, the carriers are lactose, Starch 1551, cellulose, and Povidone (PVP). Most preferably, the carriers are lactose, cellulose and Starch 1551.

Preferably, the carriers used in the wet granulation process are present in 0–70% on a weight for weight basis depending on the unit dose strength of eprosartan required. Most preferably, the carriers may be present at as low as 0–7% on a weight for weight basis in order to produce granulations with a high drug load.

The process for preparing the solid dosage forms in accordance with the present invention may be carried out using a planetary mixture, a V-blender, a high shear granulator, a fluid bed granulator or a tableting machine. Optionally, the anhydrous form of (E)-α-[2-n-butyl-1-[(4-carboxyphenyl)methyl]-1H-imidazol-5-yl]methylene-2-thiophenepropionic acid arginyl charge-neutralization-complex may be granulated first with a suitable excipient using a conventional granulating equipment, said excipient stabilizing the charge-neutralization-complex which is formed in about 2–10 minutes (time duration for a high shear granulation). Optionally, drying of the granulation may be avoided by using less water at the granulation stage, and the granulation thus produced is suitable for the preparation of direct compression immediate or modified release dosage forms. The wet and dry granulations may be filled into hard gelatin capsules or compressed into tablets. Optionally, the immediate release tablet cores may be coated with a membrane of a polymer imparting delayed or sustained release properties. For example, the capsules or tablets may be coated with a battery of sustained/modified release or enteric polymers to produce targeted release dosage forms.

Thus, the present invention provides a pharmaceutical composition which comprises (E)-α-[2-n-butyl-1-[(4-carboxyphenyl)methyl]-1H-imidazol-5-yl]methylene-2-thiophenepropionic acid arginyl charge-neutralization-complex and a pharmaceutically acceptable carrier. The pharmaceutical composition is adapted for oral administration. The composition is presented as a unit dose pharmaceutical composition containing from about 50 mg to about 1.0 g of (E)-α-[2-n-butyl-1-[(4-carboxyphenyl)methyl]-1H-imidazol-5-yl]methylene-2-thiophenepropionic acid arginyl charge-neutralization-complex, preferably from about 200 to about 400 mg. Such a composition is normally taken from 1 to 4 times daily, preferably from 1 to 2 times daily. The preferred unit dosage forms include tablets or capsules. The compositions of this invention may be formulated by conventional methods of admixture such as blending, filling and compressing. Suitable pharmaceutically acceptable carriers for use in this invention include diluents, fillers, binders and disintegrants.

(E)-α-[2-n-Butyl-1-[(4-carboxyphenyl)methyl]-1H-imidazol-5-yl]methylene-2-thiophenepropionic acid arginyl charge-neutralization-complex may be co-administered with other pharmaceutically active compounds, for example, in physical combination or by sequential administration. Conveniently, the compound of this invention and the other active compound are formulated in a pharmaceutical composition. Thus, this invention also relates to pharmaceutical compositions comprising (E)-α-[2-n-butyl-1-[(4-carboxyphenyl)methyl]-1H-imidazol-5-yl]methylene-2-thiophenepropionic acid arginyl charge-neutralization-complex, a pharmaceutically acceptable carrier, and a second pharmaceutically active compound selected from the group consisting of a diuretic, a calcium channel blocker, a β-adrenoceptor blocker, a renin inhibitor, and an angiotensin converting enzyme inhibitor. Examples of compounds which may be included in pharmaceutical compositions in combination with (E)-α-[2-n-butyl-1-[(4-carboxyphenyl)methyl]-1H-imidazol-5-yl]methylene-2-thiophenepropionic acid arginyl charge-neutralization-complex are diuretics, particularly a thiazide diuretic, such as hydrochlorothiazide, or a loop diuretic, such as furosemide, calcium channel blockers, particularly dihydropyridine antagonists, such as nifedipine, β-adrenoceptor blockers, such as propranolol, renin inhibitors, such as enalkinen, and angiotensin converting enzyme inhibitors, such as captopril or enalapril. Preferably, the pharmaceutical composition contains 200–400 mg of (E)-α-[2-n-butyl-1-[(4-carboxyphenyl)-methyl]-1H-imidazol-5-yl]methylene-2-thiophenepropionic acid arginyl charge-neutralization-complex in combination with 6.25–25 mg of hydrochlorothiazide.

No unacceptable toxicological effects are expected when (E)-α-[2-n-butyl-1-[(4-carboxyphenyl)methyl]-1H-imidazol-5-yl]methylene-2-thiophenepropionic acid arginyl charge-neutralization-complex is administered in accordance with the present invention.

(E)-α-[2-n-Butyl-1-[(4-carboxyphenyl)methyl]-1H-imidazol-5-yl]methylene-2-thiophenepropionic acid arginyl charge-neutralization-complex is useful for treating diseases in which blockade of the angiotensin II receptor would be beneficial. Preferably, this compound is used alone or in combination with said second pharmaceutically active compounds in the treatment of hypertension, congestive heart failure and renal failure. Additionally, (E)-α-[2-n-butyl-1-[(4-carboxy-phenyl)methyl]-1H-imidazol-5-yl]methylene-2-thiophenepropionic acid arginyl charge-neutralization-complex is of value in the treatment of left ventricular hypertrophy regression, diabetic nephropathy, diabetic retinopathy, mascular degeneration, haemorrhagic stroke, primary and secondary prevention of infarction, prevention of atheroma progression and the regression of atheroma, prevention of restinosis after angioplasty or bypass surgery, improving cognitive function, angina, glaucoma, and CNS disorders, such as anxiety.

The following examples are illustrative of the instant invention. These examples are not intended to limit the scope of this invention as defined hereinabove and as claimed hereinbelow.

In Examples 1–13 below, the term "internals" means the ingredients which are granulated and the term "externals" means the ingredients which are blended with the granulation.

EXAMPLES

Examples 1–2

Preparation and Formulation of (E)-α-[2-n-Butyl-1-[(4-carboxyphenyl)methyl]-1H-imidazol-5-yl]methylene-2-thiophenepropionic Acid Arginyl Charge-neutralization-complex

TABLE II

Formulation Summary

| | Example 1 (%) | Example 2 (%) |
|---|---|---|
| Internals | | |
| Compound A* | 30–75 | 30–5** |
| L-Arginine | 10–25 | 10–25 |
| Purified water | *** | *** |
| Externals | | |
| Avicel PH102 | 10–20 | 10–20 |
| Mag. stearate | 0.5–1.5 | 0.5–1.5 |

*(E)-α-[2-n-butyl-1-[(4-carboxyphenyl)methyl]-1H-imidazol-5-yl]methylene-2-thiophenepropionic acid monomethanesulfonate, anhydrous form
**(E)-α-[2-n-butyl-1-[(4-carboxyphenyl)methyl]-1H-imidazol-5-yl]methylene-2-thiophenepropionic acid (zwitterion)
*** Composition does not take into account the formation of the charge-neutralization-complex during granulation.

Table II, above, summarizes the amounts of Compound A and carriers on a weight for weight basis used in the formulations detailed in Examples 1–2 below.

Example 1

A Collette high shear granulator, is charged with the anhydrous form of (E)-α-[2-n-butyl-1-[(4-carboxyphenyl)methyl]-1H-imidazol-5-yl]methylene-2-thiophenepropionic acid monomethanesulfonate and L-arginine, and granulated for 10 min by adding water (added in parts) at a low speed and low chopper setting followed by mixing for 2 minutes at high speed and high chopper setting. The granulate is then milled through an appropriate screen and dried to an LOD of 1.5 to 3.0%. The dried granulate is milled or seived. The seived granules have been shown to contain the arginyl charge-neutralization-complex. The sieved granules are either filled into hard gelatin capsules with or without mixing blended externals or compressed into tablets. The tablets and the contents of the capsules have been shown to contain the drug substance as the arginyl charge-neutralization-complex.

Example 2

Anhydrous form of (E)-α-[2-n-butyl-1-[(4-carboxyphenyl)methyl]-1H-imidazol-5-yl]methylene-2-thiophenepropionic acid (zwitterion) and L-arginine, are mixed and granulated in a mortar and pestle by adding water (added in parts) and mixing constantly until proper wet mass is obtained. The granulate is then milled through an appropriate screen and dried to an LOD of 1.5 to 3.0%. The dried granulate is milled or sieved. The sieved granules have been shown to contain the arginyl charge-neutralization-complex.

Examples 3–7

Preparation and Formulation of (E)-α-[2-n-Butyl-1-[(4-carboxyphenyl)methyl]-1H-imidazol-5-yl]methylene-2-thiophenepropionic Acid Arginyl Charge-neutralization-complex

TABLE III

Formulation Summary

| | Example 3 (%) | Example 4 (%) | Example 5 (%) | Example 6 (%) | Example 7 (%) |
|---|---|---|---|---|---|
| Internal granules | | | | | |
| Compound A* | 50 | 49 | 48 | 47.5 | 47.5 |
| L-Arginine | 50 | 49 | 48 | 47.5 | 47.5 |
| Starch 1551 | 0 | 2 | 2 | 0 | 0 |
| Avicel PH102 | 0 | 0 | 2 | 5 | 5 |
| Purified water | ** | ** | ** | ** | ** |
| Tablet Cores | | | | | |
| Internal granules | 80–96 | 80–96 | 80–96 | 80–96 | 80–96 |
| Avicel PH102 | 0–10 | 0–10 | 0–10 | 0–10 | 0–10 |
| Ac-Di-Sol | 0–4 | 0–4 | 0–4 | 0–4 | 0–4 |
| Mag. stearate | 0–1 | 0–1 | 0–1 | 0–1 | 0–1 |
| Coated Tablets | | | | | |
| Tablet Cores | per core | per core | per core | per core | per core |
| Opadry seal coat | 2–3 | 2–3 | 2–3 | 2–3 | 2–3 |
| Sureteric | 2.5–15 | 2.5–15 | 2.5–15 | 2.5–15 | 2.5–15 |
| Eudragit L30D | 2.5–15 | 2.5–15 | 2.5–15 | 2.5–15 | 2.5–15 |

*(E)-α-[2-n-butyl-1-[(4-carboxyphenyl)methyl]-1H-imidazol-5-yl]methylene-2-thiophenepropionic acid monomethanesulfonate, anhydrous form
** Composition does not take into account the formation of the charge-neutralization-complex during granulation.

The ratio 1:1 (w/w) of Eprosartan to arginine corresponds approximately to a ratio of 1:3 on a molar basis.

Table III, above, summarizes the amounts of Compound A and carriers on a weight for weight basis used in the formulations detailed in Examples 3–8 below.

Example 3

Anhydrous form of (E)-α-[2-n-butyl-1-[(4-carboxyphenyl)methyl]-1H-imidazol-5-yl]methylene-2-thiophenepropionic acid monomethanesulfonic acid salt and L-arginine, are mixed and granulated in a mortar and pestle by adding water (added in parts) and mixing constantly until proper wet mass is obtained. The granulate is then milled through an appropriate screen and dried to an LOD of 1.5 to 3.0%. The dried granulate is milled or sieved. The sieved granules have been filled into hard gelatin capsules to contain a dose equivalent to 200 mg of eprosartan per capsule. The in vitro dissolution was conducted using either USP paddle apparatus at 100 rpm or flow through dissolution apparatus at 8 mL/min flow rate using 0.05M phosphate buffer of either pH 4 or pH 5. The dissolution results are summarized in FIG. 8. A comparative bioavailability study in dogs indicated increased bioavailability of the eprosartan triarginyl formulation when administered intraduodenally as compared to the intraduodenal or peroral administration of the mesylate salt.

Examples 4–6

Either a Strea-1 Niro-aeromatic fluid bed drier or a Glatt 5/9 fluid bed granulator was used. The procesing conditions are:

| Process Parameter | Strea-1 | Glatt 5/9 |
| --- | --- | --- |
| Spray nozzle diameter | 1.2 mm | 18 mm |
| Spray rate | 8 mL/min | 50 mL/min |
| Inlet air temperature | 60° C. | 60° C. |
| Outlet air temperature | 45° C. | 45° C. |
| Atomization pressure | 1.2 bar | 2 bar |

Screen the drug and arginine through a 20 mesh screen. Charge the fluid bed drier/granulator bowl with the drug, arginine and other internal granulation carriers. Spray the water, controlling the fluidization rate appropriately. After completion of water addition, dry the granules to a final moisture content of 1.5 to 3%. Mill the granules through an appropriate screen, blend the externals and compress on a rotary tablet press using appropriate punches. The tablets were coated using a Vector mini-hi coater. The processing conditions were:

| | |
| --- | --- |
| Pan speed | 20 rpm |
| Atomization pressure | 1.1 bar |
| Spray rate: | 3 mL/min |
| Inlet air temperature | 70° C. |
| Outlet air temperature | 40° C. |
| Spray solution | 10% w/v Opadry Clear or |
| | 20% w/v Sureteric or |
| | 20% w/v Eudragit L30D |
| Number of guns | 1 |

The coating pan was loaded with tablet cores, the bed was preheated for 10 minutes and coated by spraying the coating solution. The coated tablets were tumble dried for 2 minutes after completion of the coating. The typical dissolution profiles have indicated adequate enteric protection in simulated gastric fluids (pH 1.2 and pH 2.0) for two hours and complete release in 0.05 M phosphate buffer of pH 5.0 in 30 minutes.

Example 7

Collette high shear granulator, is charged with the anhydrous form of (E)-α-[2-n-butyl-1-[(4-carboxyphenyl) methyl]-1H-imidazol-5-yl]methylene-2-thiophenepropionic acid monomethanesulfonate and L-arginine, and Avicel PH102 and granulated by adding water slowly at a high speed setting of the impellar and chopper blades until a medium granulated mass is formed. The granulate is then milled through an appropriate screen and dried to an LOD of 0.5 to 3.0%. The dried granulate is milled or seived. The seived granules have been shown to contain the drug substance as the eprosartan arginyl charge-neutralization-complex. The sieved granules are compressed into tablets. The tablet cores are then seal coated with Opadry clear and enteric coated with Sureteric. Dissolution testing was performed by using USP dissolution test for enteric coated tablets. The typical dissolution profile has indicated adequate enteric protection in simulated gastric fluid for two hours and complete release in simulated intestinal fluid in 30 minutes.

Examples 8–13

Preparation and Formulation of (E)-α-[2-n-Butyl-1-[(4-carboxyphenyl)methyl]-1H-imidazol-5-yl] methylene-2-thiophenepropionic Acid arginyl Charge-neutralization-complex

TABLE IV

| | Formulation Summary | | | | | |
| --- | --- | --- | --- | --- | --- | --- |
| | Ex. 8 (%) | Ex. 9 (%) | Ex. 10 (%) | Ex. 11 (%) | Ex. 12 (%) | Ex. 13 (%) |
| Internal granules | | | | | | |
| Compound A* | 71.2 | 71.2 | 54.9 | 54.9 | 52.18 | 53.55 |
| L-Arginine | 28.8 | 28.8 | 45.1 | 45.1 | 42.82 | 43.95 |
| Avicel PH102 | 0 | 0 | 0 | 0 | 5.0 | 2.5 |
| Purified water | ** | ** | ** | ** | ** | ** |
| Tablet Cores | | | | | | |
| Internal granules | 95.25 | 50–97 | 99.75 | 50–97 | 90–99.5 | 90–99.5 |
| Avicel PH102 | 0 | 0–40 | 0 | 0–40 | 0 | 0 |
| Ac-Di-Sol | 4 | 0–4 | 0 | 0–4 | 0–4 | 0–4 |
| Polyplasdone XL10 | 0 | 0–4 | 0 | 0–4 | 0–4 | 0–4 |
| Carbopol 971NF | 0 | 0–5 | 0 | 0 | 0 | 0 |
| Mag. stearate | 0.75 | 0–1 | 0.75 | 0–1 | 0–1 | 0–1 |

*(E)-α-[2-n-butyl-1-[(4-carboxyphenyl)methyl]-1H-imidazol-5-yl] methylene-2-thiophenepropionic acid (zwitterion), anhydrous form
** Composition does not take into account the formation of the charge-neutralization-complex during granulation.

A ratio of (53.55/43.95 w/w) of eprosartan (zwitterion) to arginine corresponds to a molar ratio of 1:3.

Table IV, above, summarizes the amounts of Compound A and carriers on a weight for weight basis used in the formulations detailed in Examples 8–13 below.

Key high shear granulator, is charged with the anhydrous form of (E)-α-[2-n-butyl-1-[(4-carboxyphenyl)methyl]-1H-imidazol-5-yl]methylene-2-thiophenepropionic acid (zwitterion) and L-arginine, and Avicel PH102 (in examples 12 and 13) and granulated by adding water slowly at a high speed setting of the impellar and chopper blades until a medium granulated mass is formed. The granulate is then milled through an appropriate screen and dried to an LOD of 0.5 to 3.0%. The dried granulate is milled or seived. The seived granules have been shown to contain the arginyl charge-neutralization-complex. The sieved granules are compressed into tablets.

It is to be understood that the invention is not limited to the embodiments illustrated herein above and the right is reserved to the illustrated embodiments and all modifications coming within the scope of the following claims.

What is claimed is:

1. A compound which is (E)-α-[2-n-butyl-1-[(4-carboxyphenyl)methyl]-1H-imidazol-5-yl]methylene-2-thiophenepropionic acid arginyl charge-neutralization-complex.

2. A process for the preparation of the compound according to claim 1 which comprises mixing (E)-α-[2-n-butyl-1-[(4-carboxyphenyl)methyl]-1H-imidazol-5-yl]methylene-2-thiophenepropionic acid or its methanesulfonate salt with L-arginine in the presence of water.

3. The process according to claim 2 wherein (E)-α-[2-n-butyl-1-[(4-carboxyphenyl)methyl]-1H-imidazol-5-yl] methylene-2-thiophenepropionic acid or its methanesulfonate salt and L-arginine are mixed in a molar ratio of 1:1 to 1:5.

4. The process according to claim 3 wherein (E)-α-[2-n-butyl-1-[(4-carboxyphenyl)methyl]-1H-imidazol-5-yl] methylene-2-thiophenepropionic acid or its methanesulfonate salt and L-arginine are mixed in a molar ratio of 1:1 to 1:3.

5. A pharmaceutical composition comprising the compound according to claim 1 and a pharmaceutically acceptable carrier.

6. A process for the preparation of the composition according to claim 5 which comprises:

(i) mixing (E)-α-[2-n-butyl-1-[(4-carboxy-phenyl) methyl]-1H-imidazol-5-yl]methylene-2-thiophenepropionic acid or its methanesulfonate and L-arginine with one or more pharmaceutically acceptable carriers;

(ii) granulating the mixture with water; and (iii) drying the granulation to a predetermined water content.

7. A process for the preparation of a solid dosage form containing the compound according to claim 1 which comprises:

(i) producing granules containing (E)-α-[2-n-butyl-1-[(4-carboxy-phenyl)methyl]-1H-imidazol-5-yl]methylene-2-thiophenepropionic acid arginyl charge-neutralization-complex; and (ii) blending said granules with other pharmaceutically acceptable carriers to be filled into a capsule or compressed into a tablet.

8. A pharmaceutical composition comprising the compound according to claim 1, a pharmaceutically acceptable carrier and a second pharmaceutically active compound selected from the group consisting of a diuretic, a calcium channel blocker, a β-adrenoceptor blocker, a renin inhibitor, and an angiotensin converting enzyme inhibitor.

9. The pharmaceutical composition according to claim 8 wherein the diuretic is hydrochlorothiazide, the loop diuretic is furosemide, the calcium channel blocker is nifedipine, β-adrenoceptor blocker is propranolol, the angiotensin converting enzyme inhibitor is captopril or enalapril, and the renin inhibitor is enalkinen.

10. A method of blocking angiotensin II receptors which comprises administering to a subject in need thereof an effective amount of the compound according to claim 1.

11. A method of treating hypertension which comprises administering to a subject in need thereof an effective amount of the compound according to claim 1.

12. A method of treating congestive heart failure which comprises administering to a subject in need thereof an effective amount of the compound according to claim 1.

13. A method of treating renal failure which comprises administering to a subject in need thereof an effective amount of the compound according to claim 1.

14. A pharmaceutical composition comprising (E)-α-[2-n-butyl-1-[(4-carboxyphenyl)methyl]-1H-imidazol-5-yl] methylene-2-thiophenepropionic acid or its methanesulfonate salt, a charge-neutralization-complexing agent and a pharmaceutically acceptable carrier.

15. The pharmaceutical composition of claim 14 wherein the charge-neutralization-complexing agent is arginine, lysine or ornithine.

16. The pharmaceutical composition of claim 15 wherein (E)-α-[2-n-butyl-1-[(4-carboxyphenyl)methyl]-1H-imidazol-5-yl]methylene-2-thiophenepropionic acid or its methanesulfonate salt and L-arginine are present in a molar ratio of 1:1 to 1:5.

17. The pharmaceutical composition of claim 16 wherein (E)-α-[2-n-butyl-1-[(4-carboxyphenyl)methyl]-1H-imidazol-5-yl]methylene-2-thiophenepropionic acid or its methanesulfonate salt and L-arginine are present in a molar ratio of 1:1 to 1:3.

* * * * *